(12) United States Patent
Carriazo

(10) Patent No.: US 6,296,650 B1
(45) Date of Patent: Oct. 2, 2001

(54) MICROKERATOME

(76) Inventor: Cesar C. Carriazo, KRA 53 #82-202 Apto 5B, Barranquilla (CO)

(*) Notice: Subject to any disclaimer, the term of this patent is extended or adjusted under 35 U.S.C. 154(b) by 0 days.

(21) Appl. No.: 09/375,154

(22) Filed: Aug. 16, 1999

Related U.S. Application Data

(60) Provisional application No. 60/128,851, filed on Apr. 12, 1999.

(51) Int. Cl.[7] .................................................. A61F 9/00
(52) U.S. Cl. ............................................................ 606/166
(58) Field of Search .................................. 606/166, 172, 606/4–5, 170–171, 167, 169, 180; 128/898

(56) References Cited

U.S. PATENT DOCUMENTS

| | | |
|---|---|---|
| Re. 35,421 | 1/1997 | Ruiz et al. . |
| 4,662,370 | 5/1987 | Hoffmann et al. . |
| 5,133,726 | 7/1992 | Ruiz et al. . |
| 5,496,339 | 3/1996 | Koepnick . |
| 5,586,980 | 12/1996 | Kremer et al. . |
| 5,624,456 | 4/1997 | Hellenkamp . |
| 5,980,543 * | 11/1999 | Carraizo et al. ............ 606/166 |
| 6,143,010 * | 11/2000 | Silvestrini et al. ............ 606/166 |

* cited by examiner

Primary Examiner—Olik Chaudhuri
Assistant Examiner—Vikki Hoa B. Trinh
(74) Attorney, Agent, or Firm—Streets & Steele; Jeffrey L. Streets

(57) ABSTRACT

A microkeratome is provided for performing a lamellar keratotomy of an ocular globe. The microkeratome includes a guide ring assembly adapted for placement on the ocular globe and suction conduit for temporarily fixing the guide ring to the ocular globe. A cutting head containing a cutting blade suitable for corneal resections is also provided. A vertical support assembly is connected to the guide ring and supports the cutting head for rotation about a horizontal axis such that rotation of the cutting head about the horizontal axis moves the cutting blade along an arcuate cutting path into engagement with the cornea of the ocular globe.

16 Claims, 12 Drawing Sheets

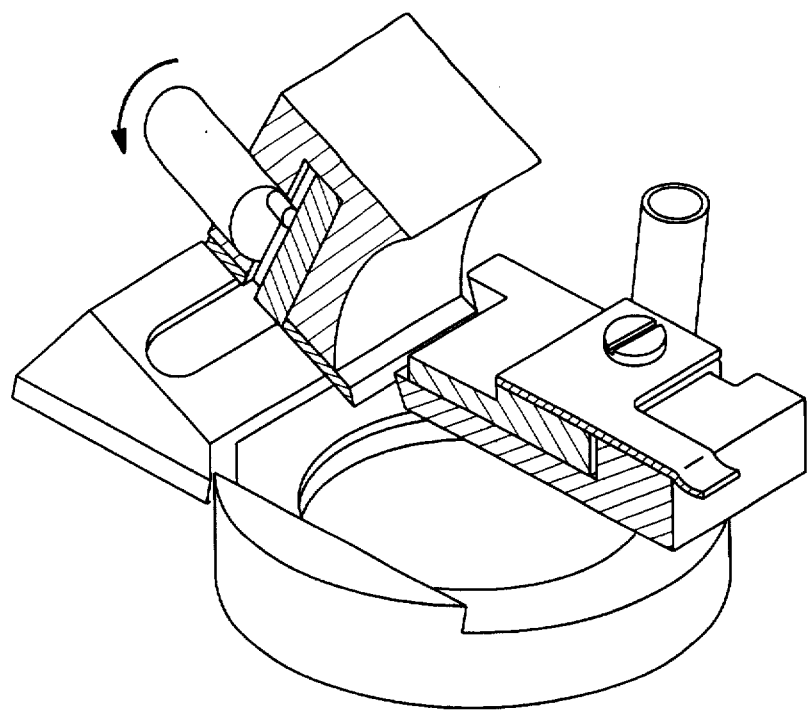
FIG. P1
(PRIOR ART)
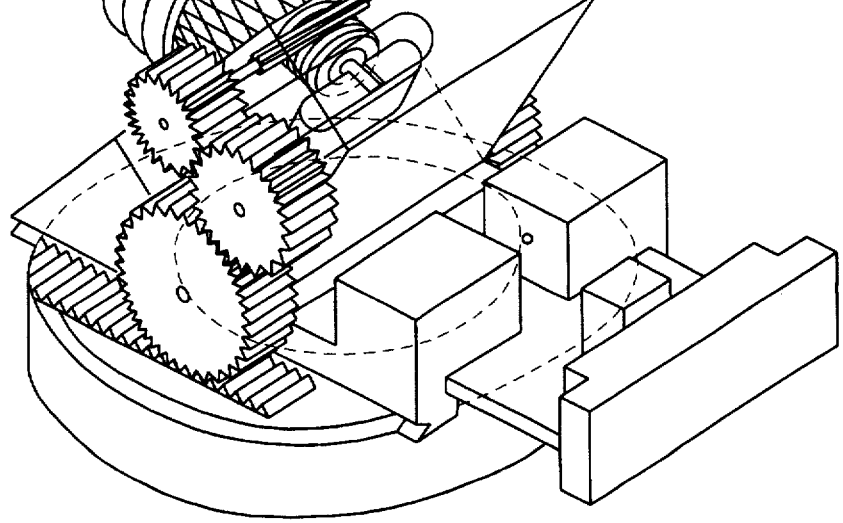
FIG. P2
(PRIOR ART)

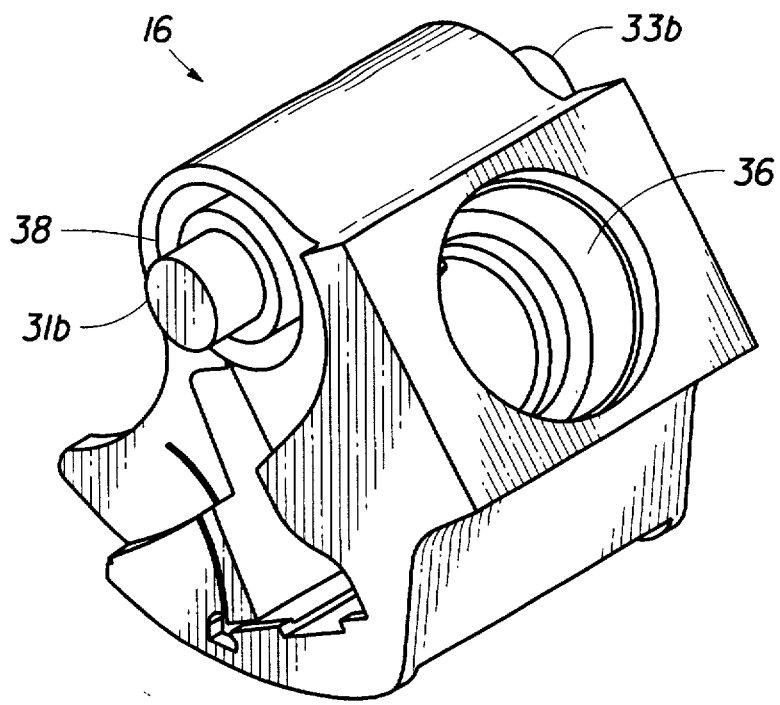
FIG. 5B
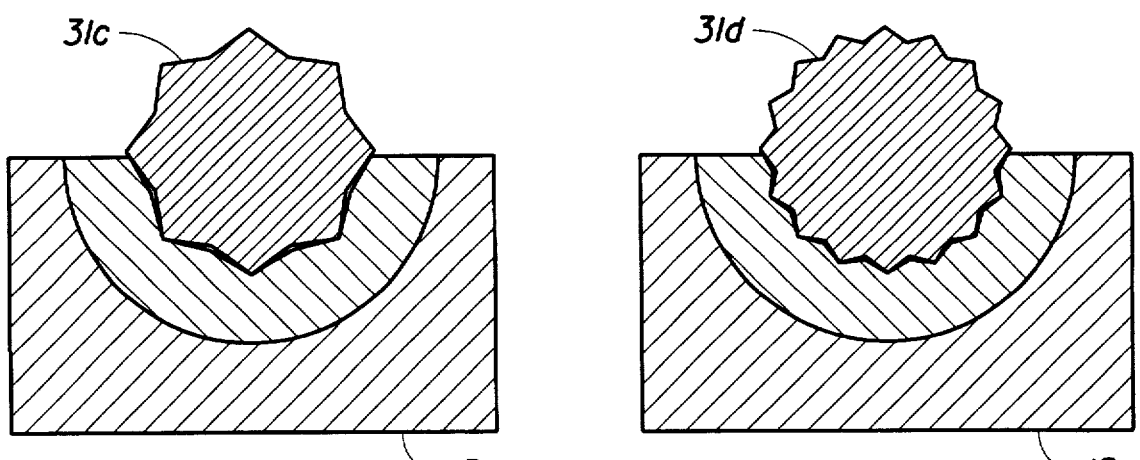
FIG. 6A
FIG. 6B

MICROKERATOME

CROSS-REFERENCE TO RELATED APPLICATION

This application claims priority to U.S. Provisional Patent Application Serial No. 60/128,851 filed on Apr. 12, 1999.

BACKGROUND OF THE INVENTION

1. Field of the Invention

The present invention relates to medical instruments and methods for performing eye surgery to correct irregularities of the cornea. More particularly, the present invention relates to mechanical instruments known as microkeratomes, and related surgical methods for performing lamellar keratotomies.

2. The Related Art

The first microkeratome for performing corneal resections was developed in 1962 by the Doctor Jose I. Barraquer, and is shown generally in FIG. P1. This microkeratome includes a guide ring which is fixed to an ocular globe, or eyeball, with the aid of a partial vacuum applied through the guide ring. The guide ring immobilizes the ocular globe, maintains the tension of the globe, and aids in regulating the diameter of the corneal resection. A portion of the microkeratome called a cutting head is supported within a channel in the guide ring for guided linear movement of the microkeratome across the ring by the surgeon. The cutting head carries a cutting blade that is oscillated by a motor-driven eccentric transverse the channel as the instrument is moved through the cutting path defined by the channel. The cutting head carries a removable, lower planar member that compresses the ocular globe ahead of the oscillating blade, to permit the blade to cut a lamella having a lower surface that is parallel to the surface of the cornea that is compressed by the planar member. The planar member is interchangeable with similar planar members of differing thicknesses, so as to vary the thickness of the resectioned corneal "disc."

Numerous variations on the Barraquer microkeratome have been made since 1962, including the apparatus that is the subject of U.S. Pat. No. 4,662,370 assigned to Carl-Zeiss-Stiftung of Germany. The '370 patent describes a microkeratome having interchangeable inserts with convex, concave, and planar surfaces that engage and compress the cornea for producing a corneal resection of predetermined form and curvature. The inserts are set within a stationary planar member that is fixed to the guide ring. The cutting blade is moved through a cutting path parallel to the planar member defined by a gap between the planar member and the guide ring, and oscillates transverse the path.

While apparently effective to permit resections of corneal lenticula, the apparatus of the '370 patent lacks means for controlling, or automating the rate of movement by the cutting head across the guide ring, and is therefore prone to binding up in the corneal tissue, or otherwise producing imprecise resections under unsteady progress by the surgeon's hand. Furthermore, there is no apparent means for changing the depth or thickness of the corneal resection. Also, this apparatus is limited to use in lamellar keratectomies (excision of a corneal section), as opposed to lamellar keratotomies (incision through the cornea).

The problem of controlled movement across the guide ring has been addressed by the instrument described in U.S. Pat. No. 5,133,726, which has been reissued as U.S. Pat. No. Re 35,421, to Luis A. Ruiz and Sergio Lenchig G. The '726 and '421 patents disclose a microkeratome, shown in FIG. P2, having a gear transmission assembly for moving the instrument through the cutting path at a controlled rate of speed. The gears are driven by the same motor that drives the cutting blade and engage a track atop the guide ring. Thus, the automated transmission system is an improvement over the instrument of the '370 patent, but in practice it has been found that the weight of the motor in the instrument produces a large moment through the handle of the device. This moment, coupled with the forward positioning of the gear that engages the guide ring track, causes the rear surface of the cutting head to bind in its engagement with the guide ring. At best, this results in uneven travel by the instrument during the surgery and unnecessary pressure fluctuations within the eye. At worst, such binding can cause irregular cutting of the cornea that produces leucoma, or the induction of an astigmatism.

The relatively recent technological development of intrastromal refractive surgery led to the creation of instruments and methods for performing incomplete lamellar temporonasal keratotomies, which leave a peripheral residue of corneal tissue uncut to act as a "nasal hinge." The nasal hinge permits the corneal disc to be lifted for exposure and carving of the stromal layer, such as by a laser. The use of a laser to perform stromal carving in association with an incomplete lamellar keratotomy is referred to as "Laser Intrastromal Keratomileusis" ("LASIK").

In similar fashion to the original Barraquer device, the microkeratome of the '726 and '421 patents include a forward planar member in the lower portion of the cutting head that is interchangeable with similar planar members of varying thicknesses. For the planar member to be interchangeable, however, a slotted portion of the cutting head extends substantially forward of the cutting blade to receive the planar member. This, and the fact that the transmission gears are positioned outside the cutting head, result in a fairly large surface area, or "footprint" for the instrument. The large footprint restricts the manner in which the microkeratome can be used, and generally requires that it be moved across the cornea from the temporal region adjacent the eye, producing the vertical nasal hinge when performing incomplete lamellar keratotomies. The vertical nasal hinge has at least two deficiencies. First, the corneal disc resulting from the LASIK, or other procedure, will be vertically displaced after surgery, and/or pleated to some extent by the opening and closing of the upper eyelid. Second, the formation of a vertical nasal hinge on the corneal disc increases the likelihood of accidental ablation of the hinge during the correction of an astigmatism, which is typically performed with horizontal cutting motions across a major diameter of the cornea.

The large surface area of the planar member, or plaque, described in the '726 patent is designed to substantially compress the entire cornea at any one time. Such action produces unnecessarily high intraocular pressure, which unduly stresses the eye and could result in complications during surgery.

Further problems with known microkeratomes have been observed in performing resections on patient's having small eyes. The smaller ocular structure, particularly the peripheral structure, of such patients presents great difficulty during a lamellar keratotomy, since a portion of the surgical instrument may collide with the ocular structure and cause surgical accidents. This problem persists because, in spite of all efforts to perform lamellar keratotomy with more reliable instruments, the physical size of the instruments and the required surface area that the instrument must occupy during a lemellar keratotomy increase the likelihood that some portion of the microkeratome structure will encounter the patient's ocular structure.

Another problem with known systems, such as the microkeratome described in U.S. Pat. No. 5,624,456, relates to the manner in which the cutting head is brought into contact with the corneal surface. More specifically, the microkeratome of the '456 patent induces movement of a cutting blade through a flat plane which is defined, by necessity, to clear the patient's ocular structure. For purposes of discussion, this plane may be considered to be a horizontal plane since the patient's head will be more or less horizontal during the procedure. In order for the cutting blade to intersect the cornea, the eye must be pulled outwardly over the ocular structures so as to place a portion of the cornea above the horizontal plane. This creates a risk of suction loss between the surgical guide ring and the eye during the operation, with potentially severe consequences.

Other problems in the related microkeratome art include the requirement of interacting drive gears which must be constantly maintained for smooth operation, and the limited options for placement of the suction orifice on the surgical guide ring. The latter problem is a result of the need to leave open a clear path or guideway in the guide ring for passage of the cutting head and cutting blade, since the cutting blade is carried in a flat, horizontal plane as described above.

It is an object of the present invention to address one or more of the shortcomings described herein, as well as others.

SUMMARY OF THE INVENTION

The objects and advantages of the present invention are achieved by an improved microkeratome for performing a lamellar keratotomy of an ocular globe. The microkeratome includes a guide ring assembly adapted for placement on the ocular globe. Means are provided for temporarily fixing the guide ring to the ocular globe. A cutting head containing a cutting blade suitable for corneal resections is also provided. A vertical support assembly is connected to the guide ring and supports the cutting head for rotation about a horizontal axis such that rotation of the cutting head about the horizontal axis moves the cutting blade along an arcuate cutting path into engagement with the cornea of the ocular globe.

In a preferred embodiment, the microkeratome includes means for rotating the cutting head about the horizontal axis to move the cutting blade at least partially through the cornea to create a corneal flap during a lamellar keratotomy. It is preferred that the rotating means includes means for inducing oscillatory motion in the cutting blade of the cutting head that is transverse the cutting path defined by rotation of the cutting head about the elevated horizontal axis.

It is also preferable that the vertical support assembly includes a pair of members extending upwardly from said guide ring 180° apart from each other.

The cutting head preferably includes a support shaft extending laterally therethrough equipped with lateral support members on either end of the support shaft that extend from opposing sides of the cutting head for engagement with the upwardly extending members of the support assembly. The lateral support members of the support shaft are sized and shaped either for static engagement with the upwardly extending members of said support assembly, whereby the support shaft is constrained against rotation relative to the upwardly extending members, or for rotational engagement with the upwardly extending members of said support assembly, whereby the support shaft is free to rotate relative to the upwardly extending members.

If the support shaft is to be constrained, it is preferred that the cutting head include an opening providing access to the support shaft, and that the rotating means include a housing adapted for connection to the cutting head at the opening therein. An output shaft is rotatably carried within the housing and has an outer portion extending from the housing for passage through the opening in the cutting head and engagement with the support shaft when the housing is connected to the cutting head. Means are carried within the housing for applying a torque to the output shaft, whereby the application of torque from the torque applying means to the output shaft induces rotation of the cutting head and the housing about the support shaft at a controlled speed.

If the support shaft is free to rotate relative to the upwardly extending members, it is preferred that the rotating means includes a housing connected to the cutting head and adapted for gripping by a surgeon to manually induce rotation of the cutting head about the elevated horizontal axis.

The microkeratome may further include stop means for limiting the range through which the cutting blade is carried by said cutting head so as to define a corneal hinge during a lamellar keratotomy.

The microkeratome may also be equipped with an adjustable float head connected to the cutting head for at least partially compressing the cornea ahead of the cutting blade so as to set the corneal resection to the desired shape and thickness. The adjustable float head preferably includes a pair of substantially parallel float arms, and a float having a multi-sided cross-section with multiple respective faces and being supported for rotation between the float arms about a journal that extends through the float. The float head may be equipped with indicia thereon for indicating the resection thickness provided by the selected face.

It is further preferred that each of the faces of the float be spaced at different distances from the journal, whereby the thickness of the corneal resection is varied by rotation of the float until the desired face is in position to compress the cornea. The float may be equipped in various ways, such as by having at least one arcuate face and/or one oblique face, whereby different corneal lenticular disc resections are performed by compressing the cornea with the respective face.

The present invention further contemplates a method of performing corneal resections for a lamellar keratotomy. A cutting head is carried for rotation about a horizontal axis elevated above the patient's eye, and rotation of the cutting head about the horizontal axis is induced to move the cutting blade through a pendular cutting path that intersects the cornea.

In one embodiment, the cutting head is supported by fixing a guide ring to an ocular globe about the globe's cornea so that the cornea extends through and above the guide ring, with the guide ring including a support system extending upwardly therefrom. The cutting head includes a support shaft adapted for alignment with the horizontal axis and constrained against rotation about the horizontal axis by the support system when the support shaft is placed in engagement with the support system. Rotation of the cutting head is induced by the operating a motor to apply a torque to the constrained support shaft to drive the cutting head and move the cutting blade through a pendular cutting path that intersects the cornea.

Preferably, the method further includes the step of stopping the movement of the cutting blade at a predetermined point along the cutting path whereby a hinged corneal cap is formed.

The presently invented method also contemplates the application of torque by automated or manual means to a cutting head carrying a cutting blade and supported for rotation about a horizontal axis elevated above the guide ring by a support system extending vertically from the guide ring, whereby the torque applied to the cutting head moves the cutting blade through a pendular cutting path that intersects the cornea.

BRIEF DESCRIPTION OF THE DRAWINGS

In the drawings, wherein like reference characters are used throughout to describe like parts:

FIG. P1 is a perspective view, partially in section, of the original Barraquer microkeratome;

Figure 1:
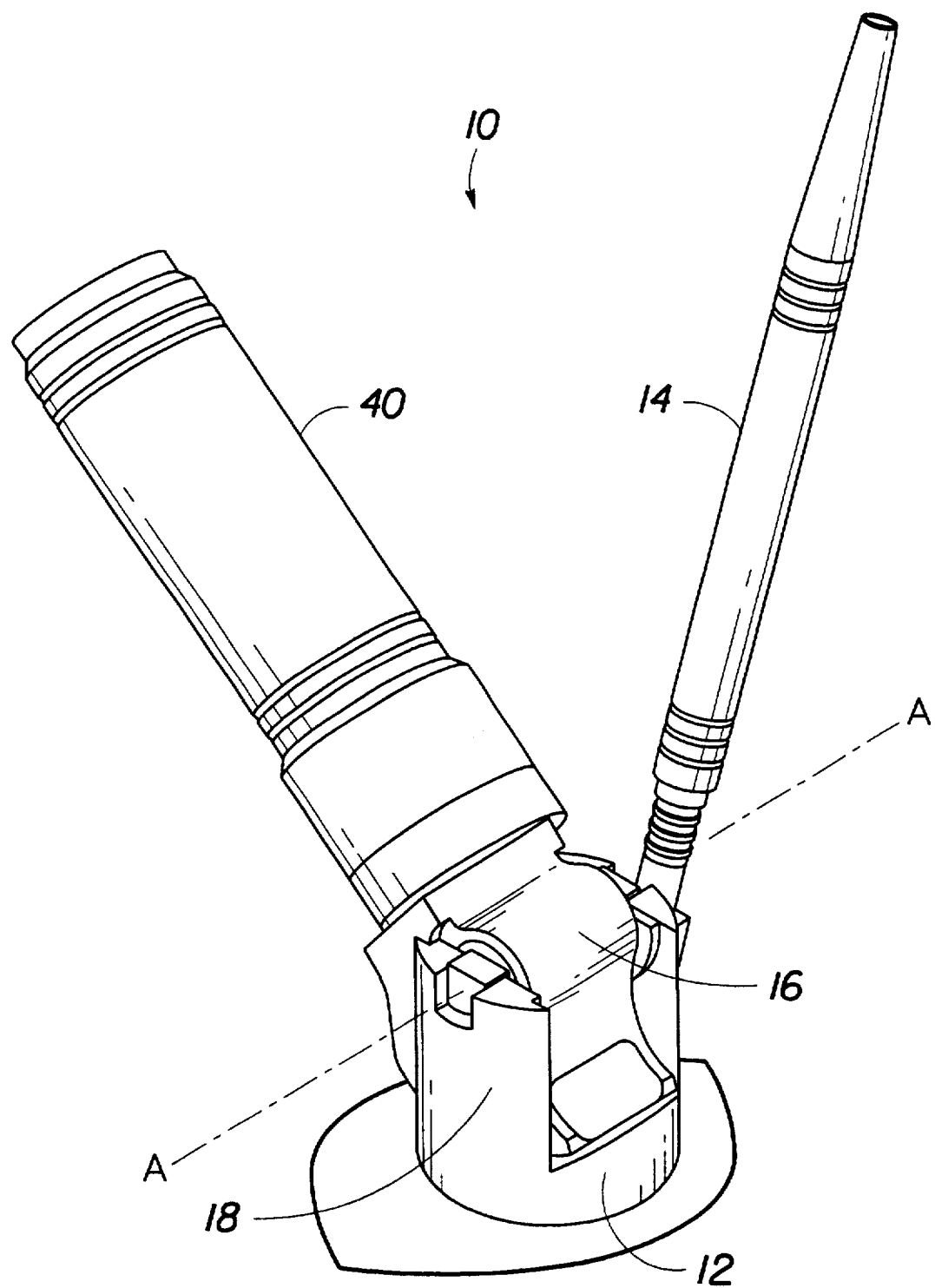
Figure 3:
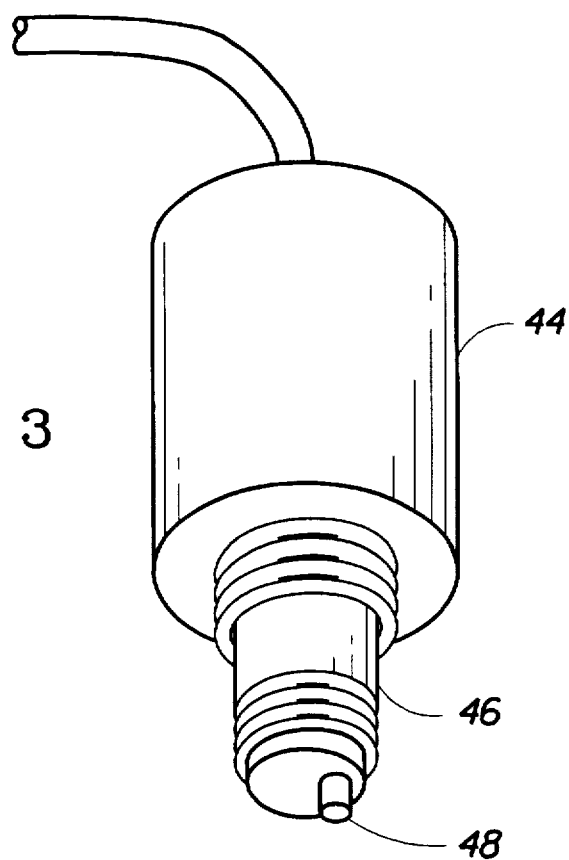
Figure 4A:
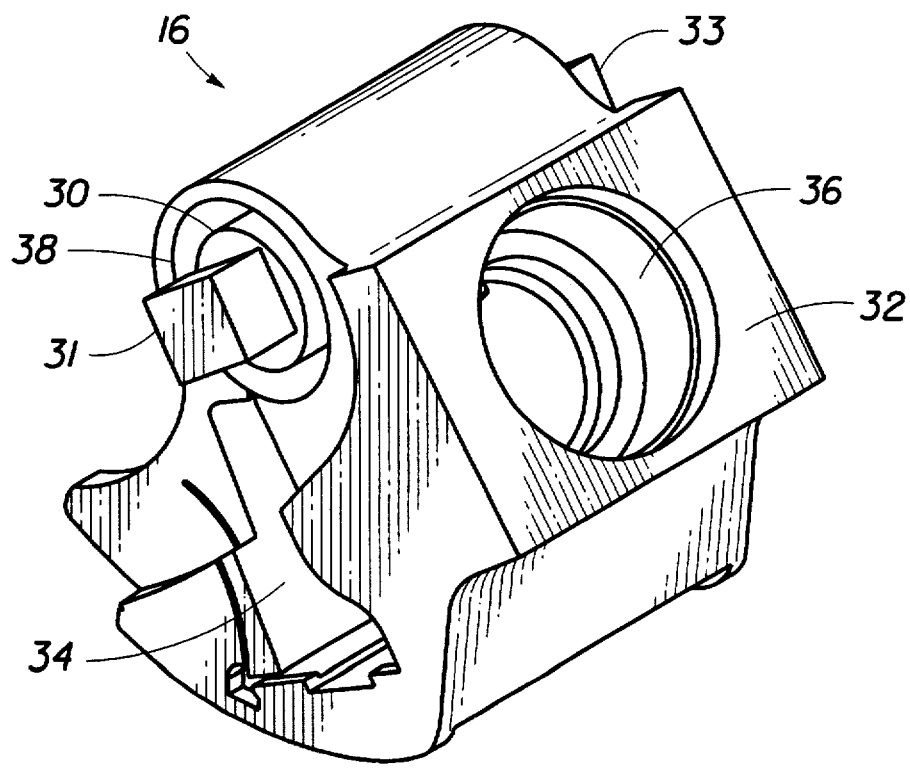
Figure 4B:
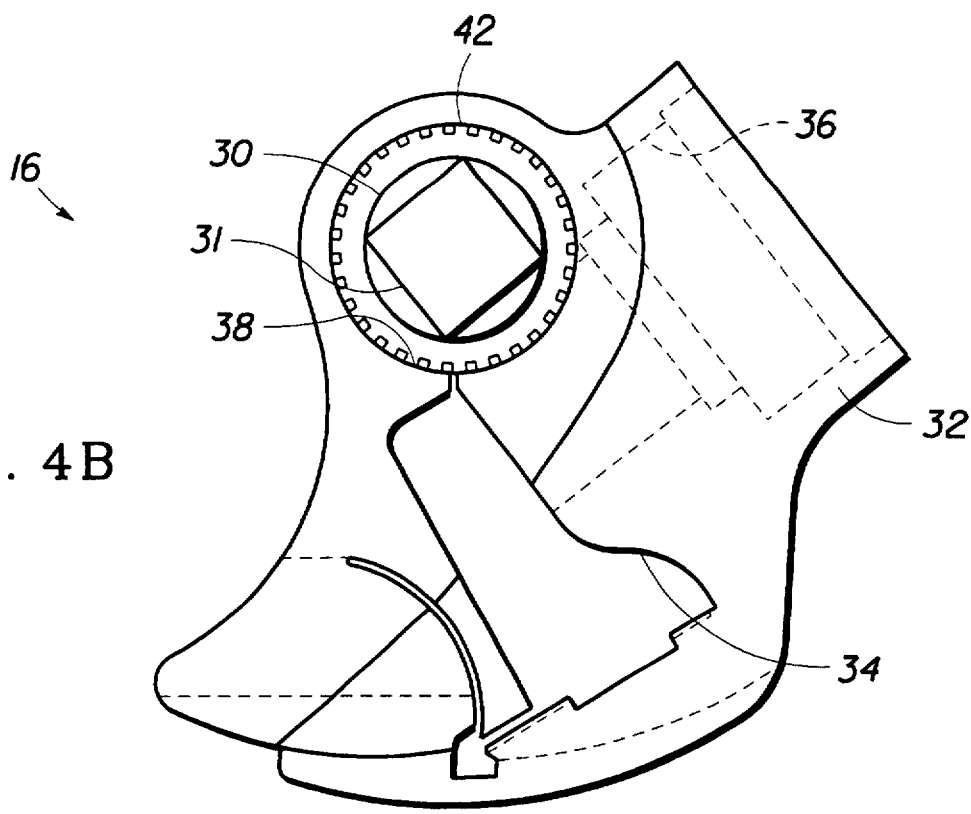
Figure 5A:
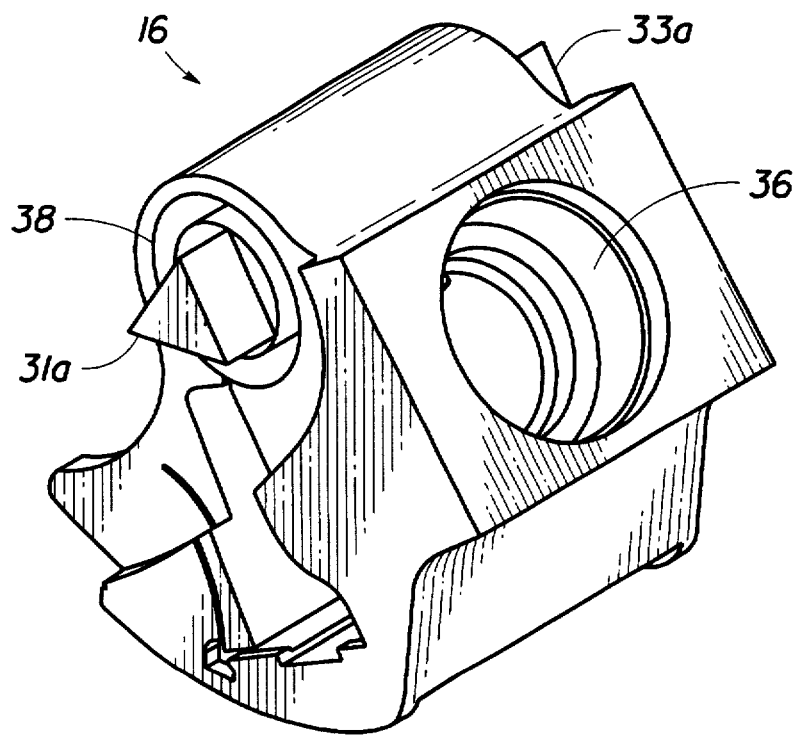
Figure 7:
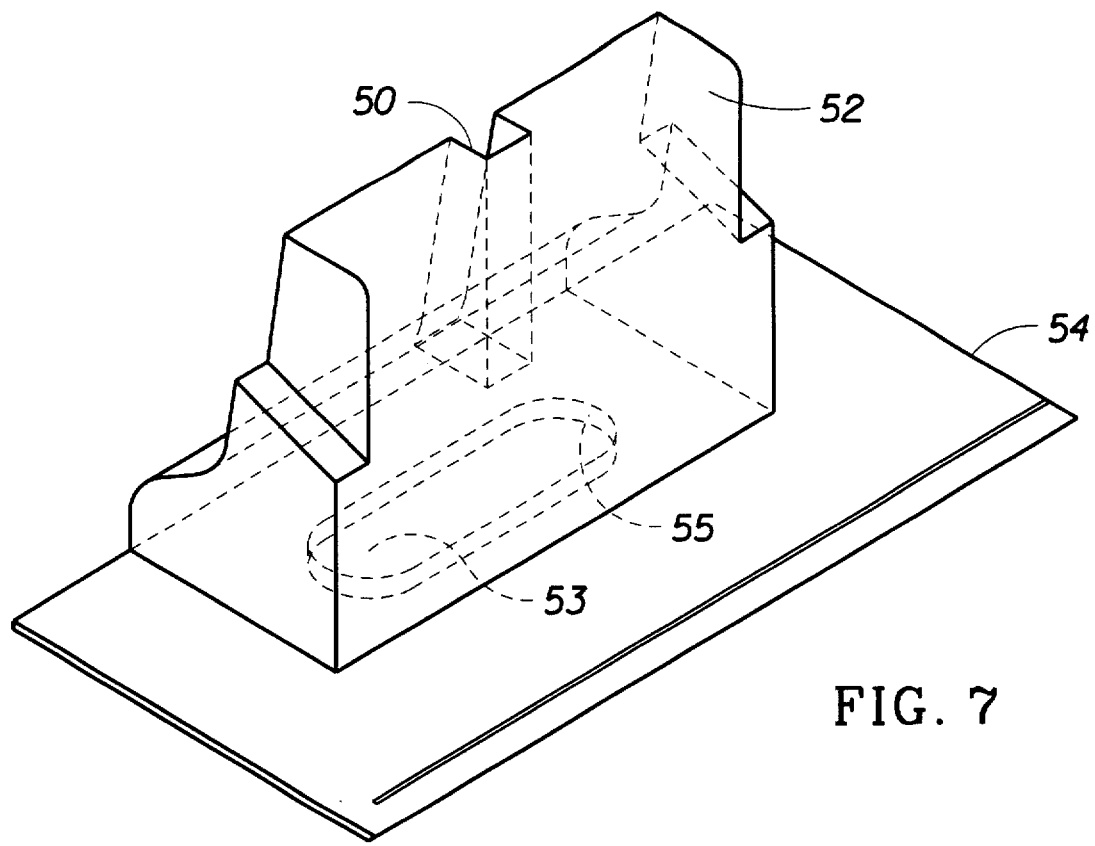
Figure 8A:
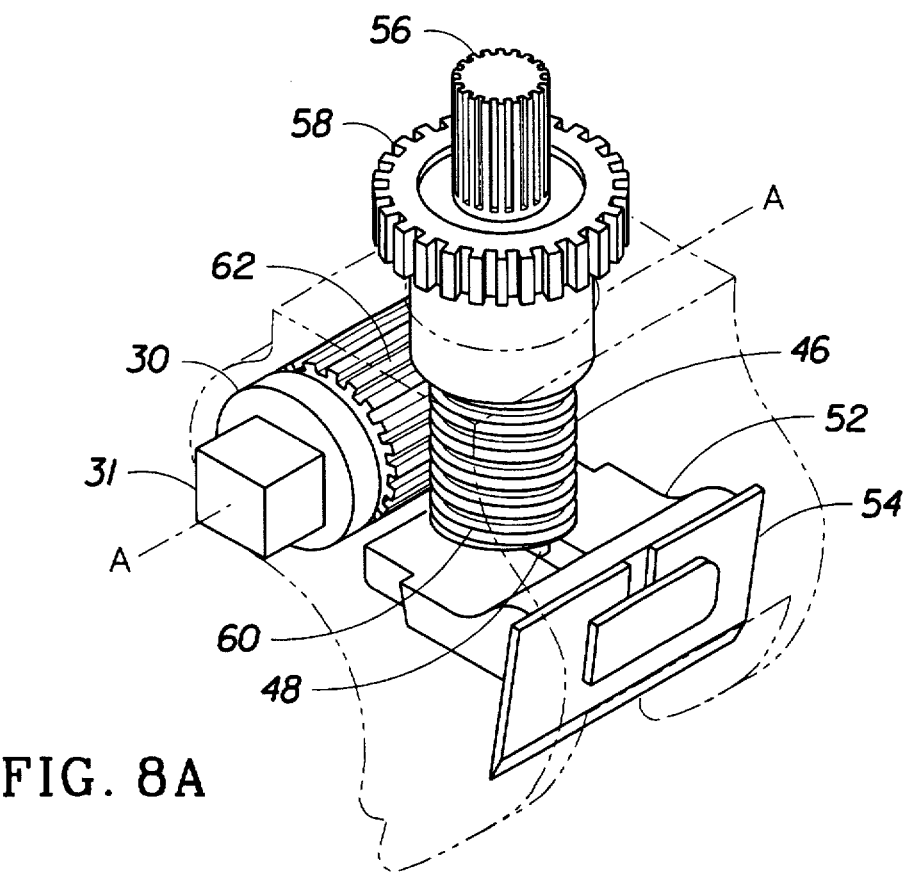
Figure 8B:
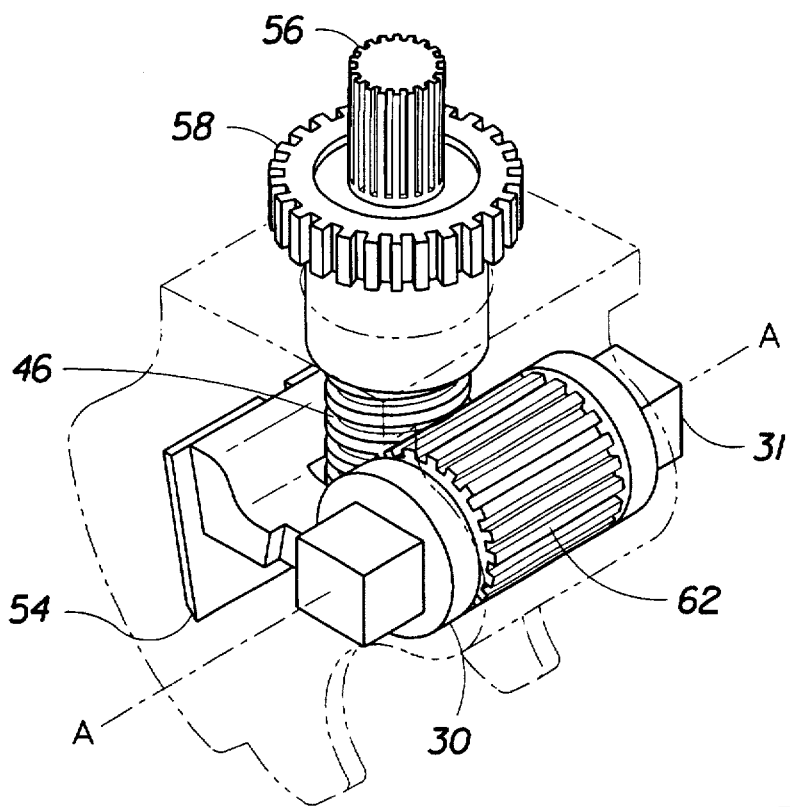
Figure 8C:
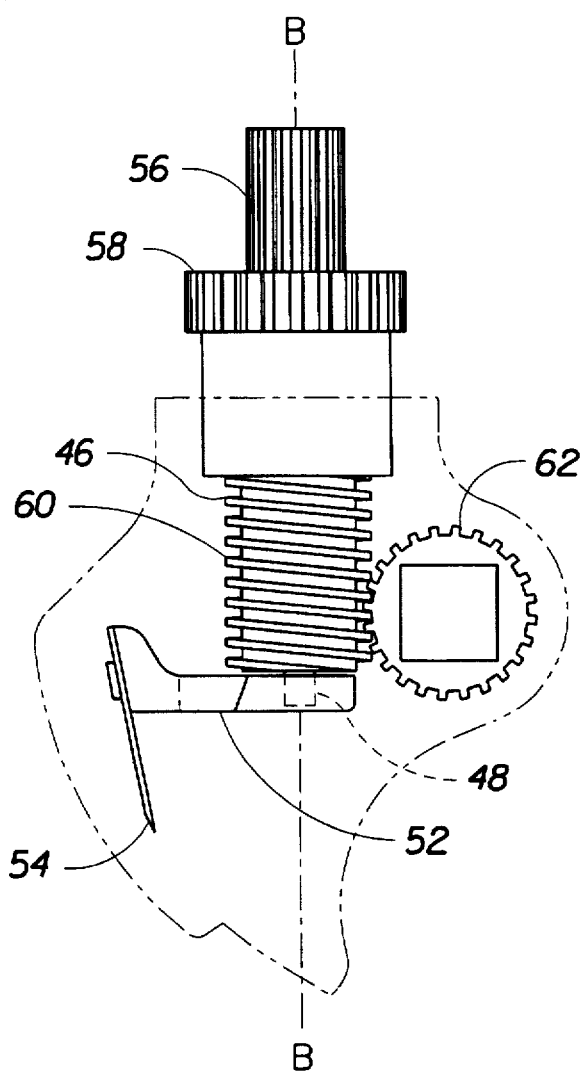
Figure 8D:
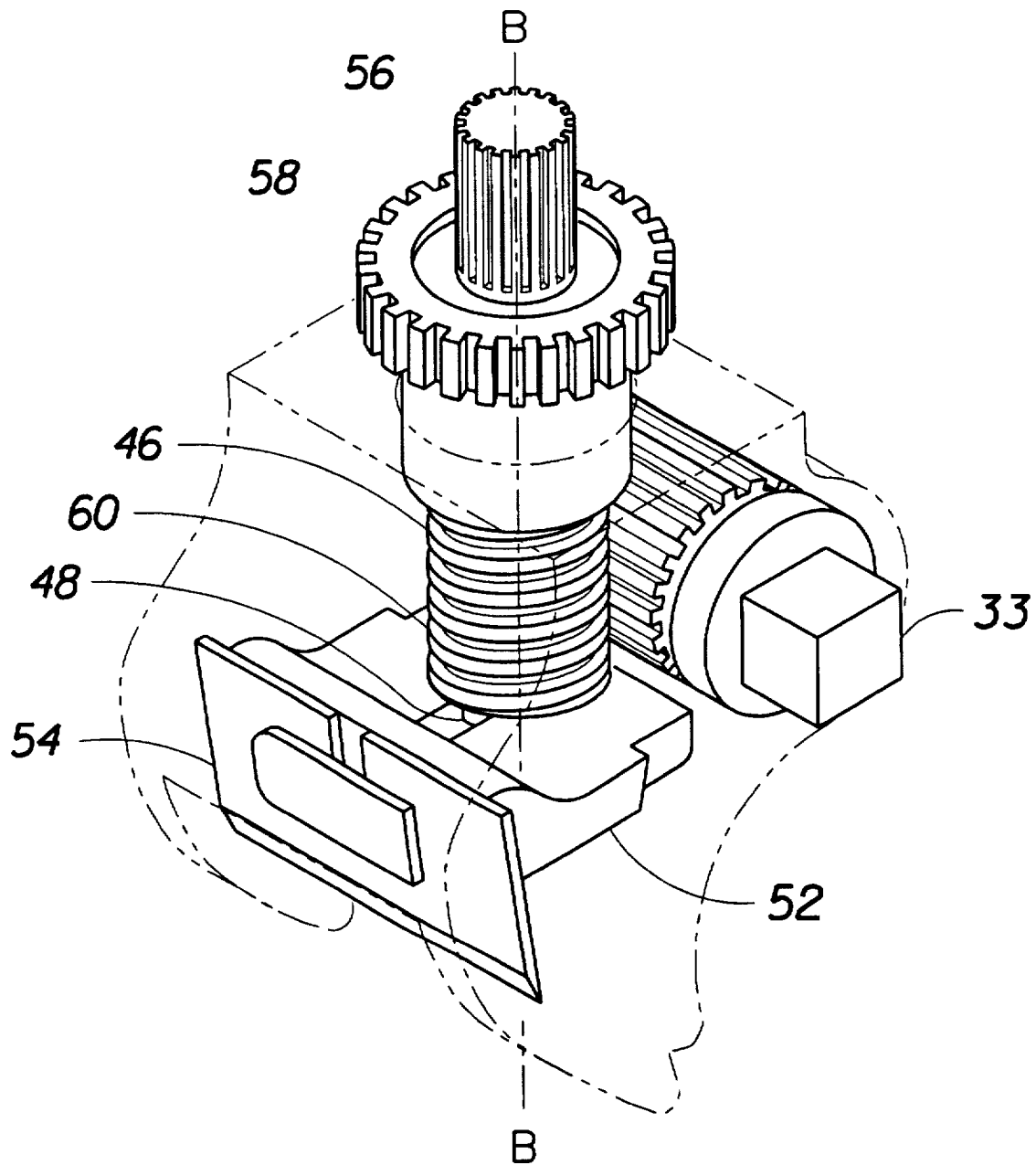
Figure 9A:
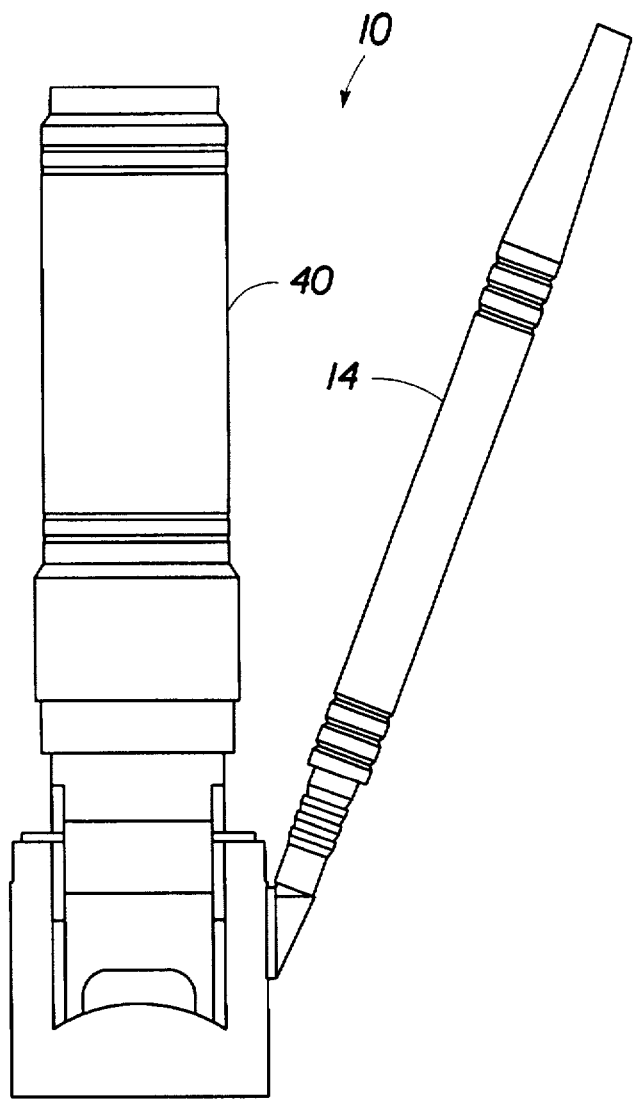
Figure 9B:
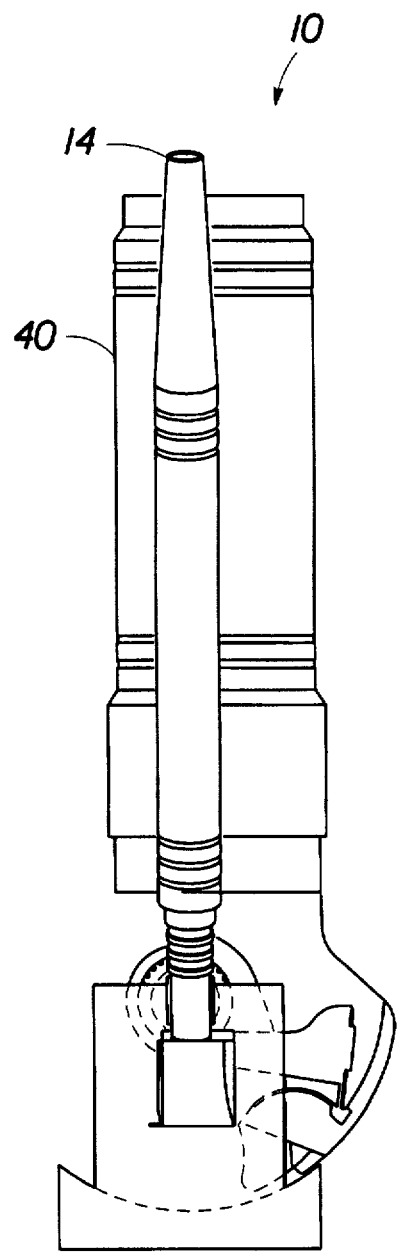
Figure 9C:
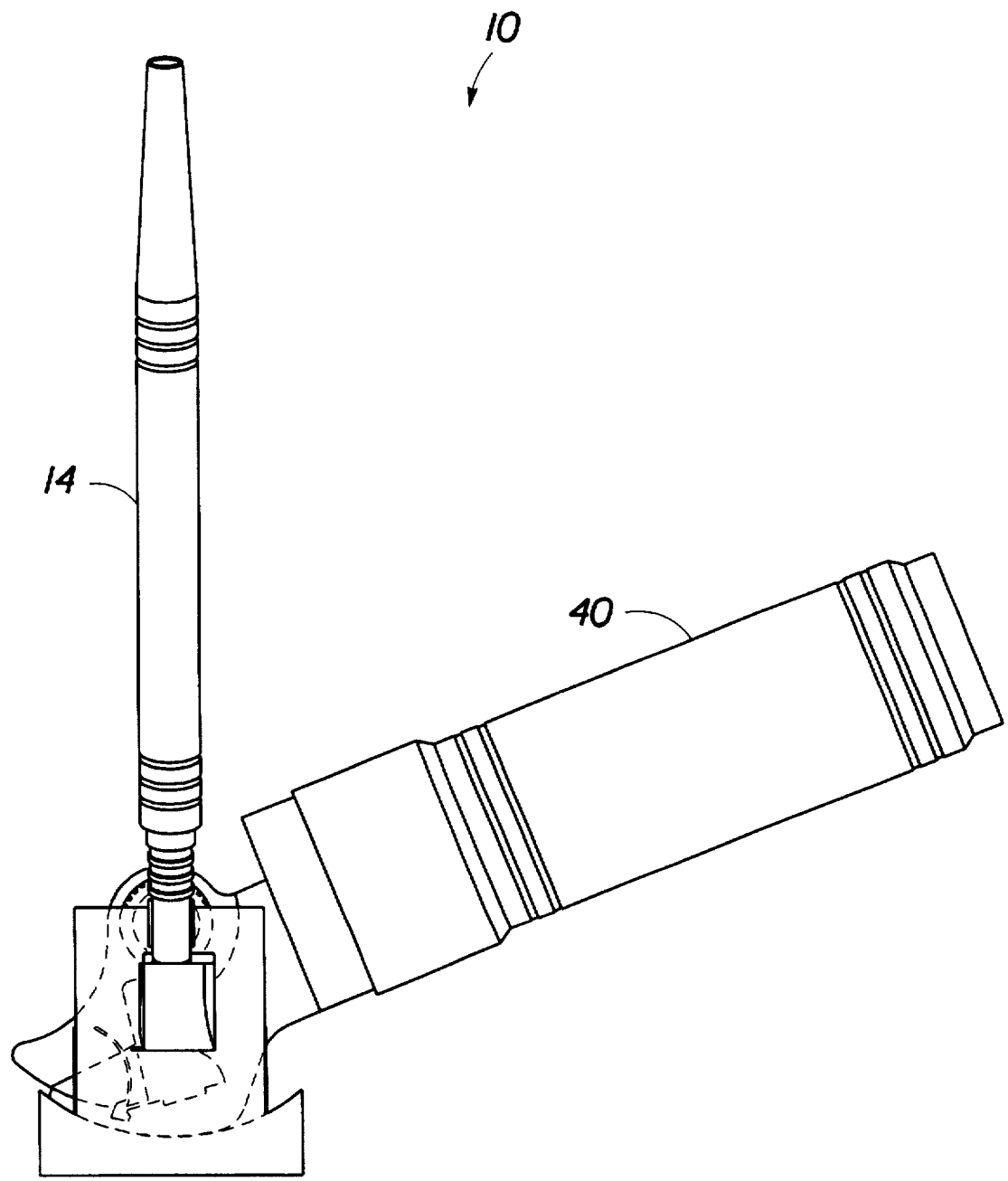

FIG. P2 is a perspective view of another prior art microkeratome;

FIG. 1 is a perspective view of a microkeratome and guide ring assembly in accordance with one embodiment of the present invention;

FIGS. 2A, 2B, 2C, and 2D are perspective, plan, frontal elevation, and side elevation views, respectively, of a vertical support assembly in accordance with the present invention;

FIG. 3 is a schematic representation of a drive motor assembly in accordance with one embodiment of the present invention;

FIGS. 4A and 4B are perspective and side elevation views of the cutting head utilized in the embodiment of FIG. 1;

FIGS. 5A and 5B are perspective views of the cutting head equipped with two alternative embodiments of a support shaft, in contrast to the support shaft shown in the cutting head of FIGS. 4A and 4B;

FIGS. 6A and 6B are side views of two additional embodiments of the cutting head support shaft;

FIG. 7 is a perspective view of a cutting blade and blade holder in accordance with the present invention;

FIGS. 8A, 8B, and 8D are perspective views, taken from different viewpoints, of the cutting head and drive gear assembly in accordance with one embodiment of the present invention;

FIG. 8C is a side view of the cutting head and drive gear assembly shown in FIGS. 8A, 8B, and 8D;

FIG. 9A is a front elevation view of one embodiment of a microkeratome and guide ring assembly in accordance with the present invention; and FIGS. 9B and 9C are side elevation views of the embodiment of FIG. 9A shown at the initial and end positions of a corneal resection.

DETAILED DESCRIPTION OF THE PREFERRED EMBODIMENTS

FIGS. 1–9C illustrate various embodiments of a microkeratome for performing a lamellar keratotomy or a lamellar keratectomy of an ocular globe, in accordance with the present invention. The instrument is suitable to perform surgery of myopia (nearsightedness), hyperopia (farsightedness), astigmatism and presbyopia (corneal stiffening due to aging), and is particularly well-suited to perform cuts other than temporo-nasal, such as bottom, upper, and oblique cuts.

With reference first to FIG. 1, microkeratome 10 generally includes guide ring assembly 12 adapted for placement directly on a patient's eye or ocular globe such that the globe's cornea protrudes therethrough. Means, including suction conduit 14, are provided for temporarily fixing guide ring 12 to the ocular globe. Cutting head 16 containing a cutting blade suitable for corneal resections is also provided, and will be discussed in greater detail below. Vertical support assembly 18 is connected to, or alternatively forms a part of, guide ring 12 and supports cutting head 16 for rotation about horizontal axis A—A elevated above guide ring 12 such that rotation of cutting head 16 about horizontal axis A—A moves a cutting blade (described below) along an arcuate cutting path into engagement with the cornea of the patient's ocular globe.

FIGS. 2A–2D illustrate guide ring 12 and vertical support assembly 18 in greater detail. Thus, vertical support assembly 18 includes a pair of arm members 20, 22 extending upwardly from guide ring 12 and spaced 180° apart from each other. By virtue of such spacing and orientation, arm members 20, 22 bound arcuate surface 24 which contains circular opening 26 permitting passage of the patient's cornea. Arm members 20 and 22 are further equipped with slots 21 and 23, respectively, for rotating cutting head 16 about axis A—A, as will be described further below.

Guide ring 12 is further equipped with vacuum adapter 28 for connection to suction conduit 14 shown in FIG. 1. The lower portion of guide ring 12 defines suction ring 13 which conducts partial vacuum (below atmospheric) pressure delivered through suction conduit 14 and vacuum adapter 28 from a vacuum pump (not shown) to the patient's ocular globe or eyeball. In this manner, the eyeball is immobilized relative to the guide ring and the intraocular pressure is regulated.

Cutting head 16 is shown in greater detail in FIGS. 4A–5B. The cutting head includes support shaft 30 which extends laterally through body 32. Support shaft 30 is equipped with lateral support members 31, 33 on either end thereof that extend from opposing sides of cutting head body 32 for engagement with slots 21, 23, respectively, of upwardly extending arm members 20, 22 of the support assembly, as seen in FIGS. 2A–2B.

Figure 2A:
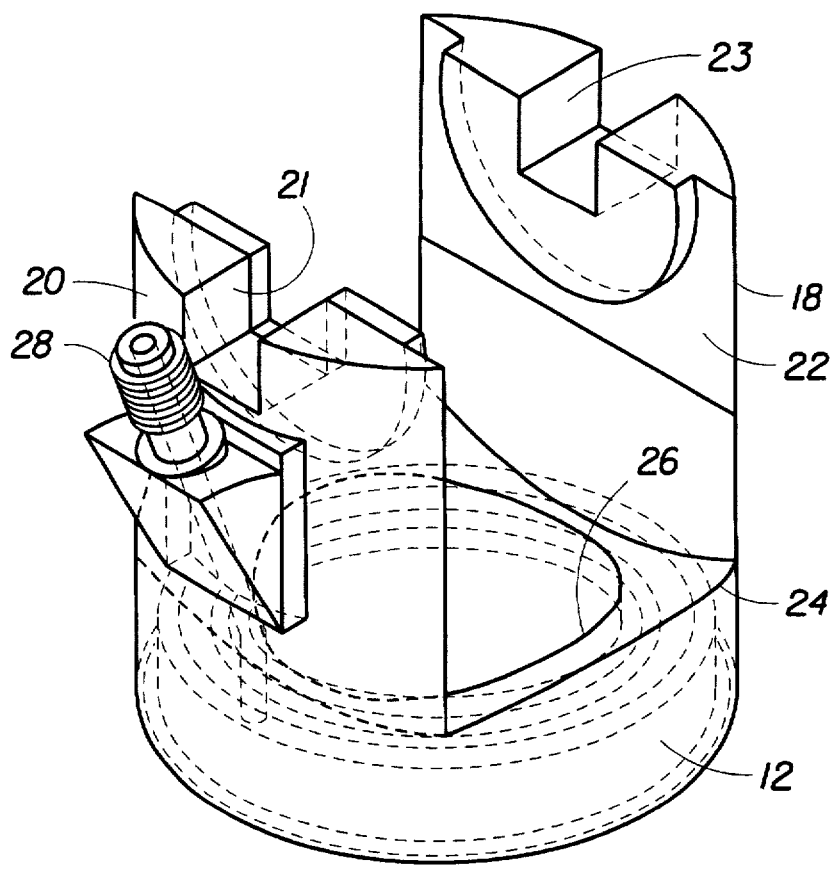
Figure 2B:
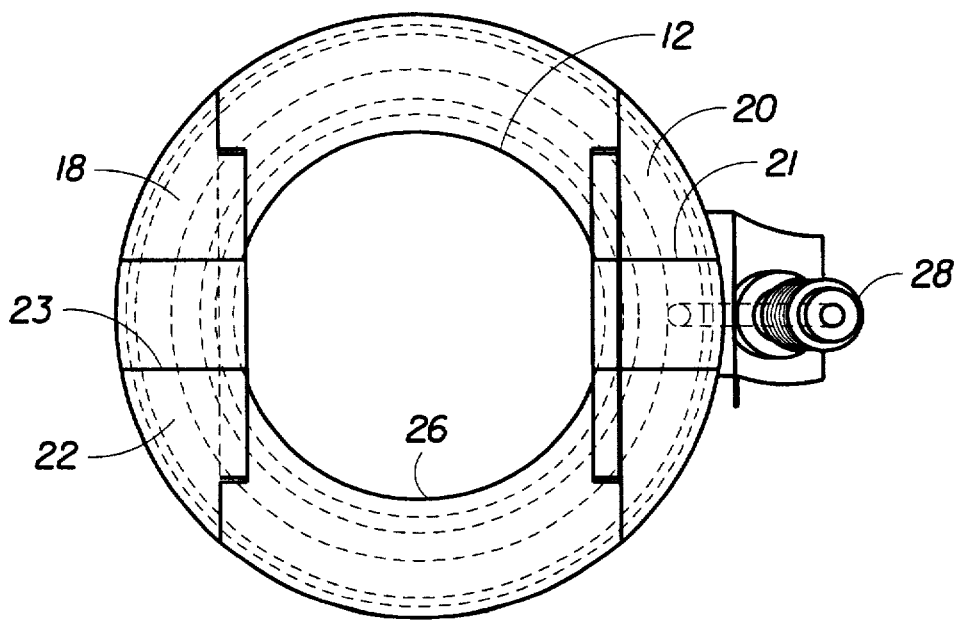
Figure 2C:
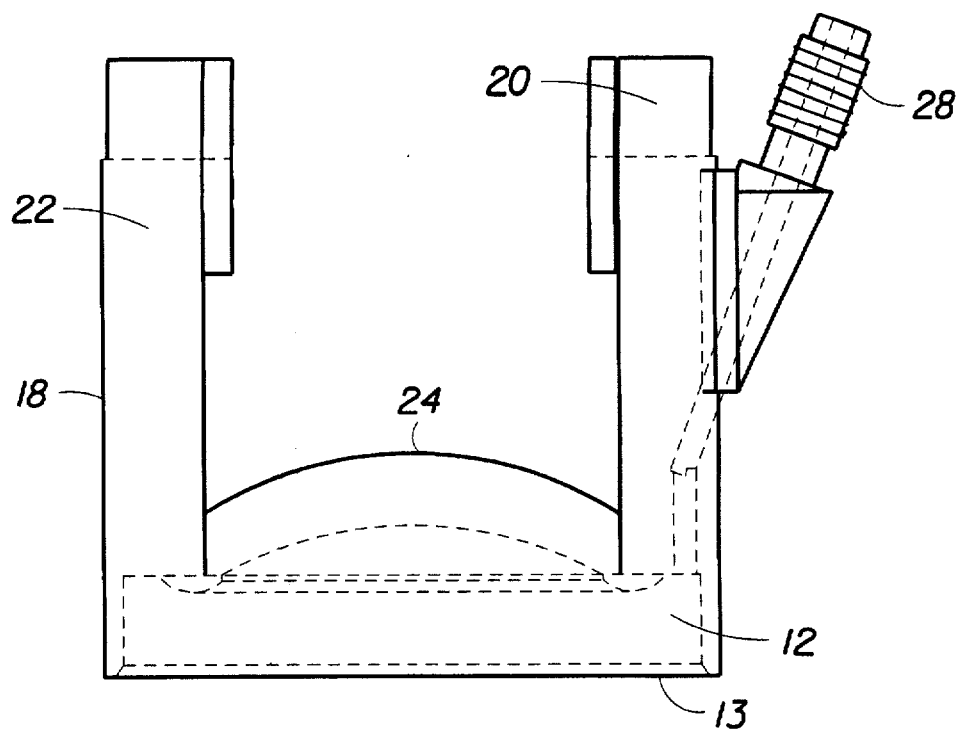
Figure 2D:
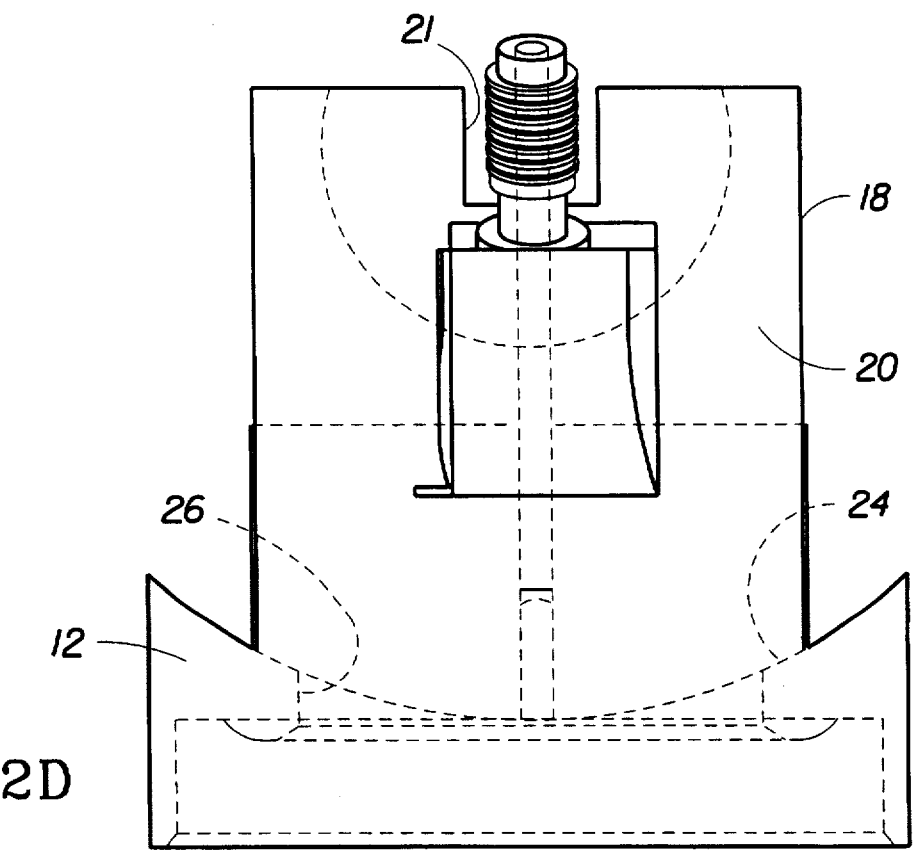

Referring back to FIGS. 4A–4B, as well as FIGS. 2A–2B, lateral support members 31, 33 of support shaft 30 are square-shaped and sized for closely fitting within U-shaped square slots 21, 23 defined by arm members 20, 22 of vertical support assembly 18. In this manner, support shaft 30 of cutting head 16 is placed in static engagement with arm members 20, 22 whereby the support shaft is constrained against rotation relative to vertical support assembly 18 and guide ring 12.

FIG. 5A illustrates an alternative embodiment wherein support shaft 30 terminates in triangular-shaped lateral support members 31a, 33a for static engagement (not shown) with the upwardly extending arm members of the vertical support assembly. Those skilled in the art will appreciate that the arm members of this embodiment will define V-shaped slots sized for a close fit with support members 31a, 33a.

FIG. 5B illustrates another alternative embodiment wherein support shaft 30 terminates in circular-shaped lateral support members 31b, 33b for rotational engagement (not shown) with the upwardly extending members of the vertical support assembly whereby the support shaft is free to rotate relative to the upwardly extending arm members. In this embodiment, the arm members will define semi-circular openings for a close fit with support members 31b, 33b.

The embodiment of cutting head body 32 shown in FIGS. 4A–5B is a uni-body of cast construction having a side opening therein for moving a blade and blade holder assembly through cavity 34. In addition to cavity 34, cutting head 32 includes substantially cylindrical opening 36 of variable bore size and depth, as well as lateral cylindrical bore 38 therein. Opening 36 is formed with either threads or a mechanical slot for engagement with complementary threads or mechanical key on handle 40 of microkeratome 10. The action of a drive motor carried within handle 40 in one embodiment of the present invention will be explained below.

Lateral bore 38 is sized for accepting shaft 30 having outer threads 42 and support members 31, 33, which are square-shaped as indicated in FIGS. 4A and 4B. These support members may alternatively be triangular as seen at 31a and 33a in FIG. 5A, circular as seen at 31b and 33b in FIG. 5B, or star-shaped as seen at 31c and 31d in FIGS. 6A and 6B.

The cutting head may be further equipped with upper and lower portions connected by a hinge (not shown) that permits the cutting bead to be opened for accessing the cutting blade. Alternatively, the cutting head may be equipped with first and second laterally connected portions for the same purpose.

Microkeratome 10 further includes means for rotating cutting head 16 about elevated horizontal axis A—A to move the cutting blade at least partially through the cornea to create a corneal flap during a lamellar keratotomy. The rotating means includes, in at least one embodiment of the present invention, means for inducing oscillatory motion in the cutting blade of the cutting head that is transverse the cutting path defined by rotation of the cutting head about the elevated horizontal axis.

With reference now to schematic representation of FIG. 3, electric drive motor 44, or other similar means provides the torque necessary for rotating input shaft 46, which terminates outside the motor housing in small eccentric projection or pin 48. As indicated by the gear arrangement shown in FIGS. 8A and 8B, torque from drive motor 21 may be applied to either of gears 56, 58 mounted to shaft 46 or otherwise applied directly to the shaft which rotates pin 48. The assembly of drive motor 44 and input shaft 46 is mounted within handle 40 in such a manner that, when handle 40 is engaged with cutting head 16, eccentric pin 48 engages slot 50 of blade holder 52, seen in FIG. 7, to transmit an oscillatory motion to blade 54 that corresponds to the speed of the motor. This arrangement of blade holder 52, blade 54, and eccentric pin 48 is shown in FIGS. 8A–8D.

Cutting blade 54 is rectangular and includes elongated slot 55 that closely fits over projection 53 of blade holder 52 to mount the blade to the blade holder within the cutting head. As mentioned above, blade holder 54 has vertical rectangular groove 50 therein for engagement by eccentric pin 48 of shaft 46 through cylindrical cavity 36 of the cutting head. As the eccentric pin is rotated off-center by shaft 46, it induces back-and-forth lateral motion of blade holder 52 within cavity 34 of the cutting head. This lateral motion results in the oscillation of blade 54.

Rotation of input shaft 46 also rotates external threads 60 thereon about axis B—B, which, in the embodiment of FIGS. 8A–8D, induces rotation of cutting head 16 about axis A—A. More particularly, threaded portion 60 of shaft 46 engages outer threads 62 of shaft 30. Since shaft 30 is constrained against rotation by the engagement of support members 31 and 33 in openings 31 and 33, respectively, of support assembly 18, the torque of input shaft 46 induces the input shaft, motor 44, handle 40, and cutting head 16 to all rotate as a unit about axis A—A. In this manner, the cutting blade (described below) cuts at least partially through the cornea to perform the desired lamellar keratotomy.

Threaded sections 60 and 62 may be of various diameters so as to provide for speed adjustments therebetween, in other words, step-down, step-up, or constant speed, between the rate of blade oscillation and the rate of cutting head rotation about axis A—A. Thus, these rates may be 1:1, or the speed of the blade oscillation may be designed to be faster or slower than the speed of cutting head rotation about axis A—A.

If support shaft 30 is instead free to rotate relative to upwardly extending members 18, as in the embodiment of FIG. 5B, the means for rotating cutting head 16 will include a handle (not unlike handle 40) connected to the cutting head, which is adapted for gripping by a surgeon to manually induce rotation of the cutting head about the elevated horizontal axis. Those skilled in the art will appreciate that this manually driven embodiment can also be equipped with drive motor 44 for inducing the transverse oscillatory motion of blade 54 as the blade is moved through the cornea. Such oscillatory motion promotes a smooth, continuous cut through the corneal tissue.

The microkeratome may further include a stop means (not shown) for limiting the range through which the cutting blade is carried by said cutting head so as to define a corneal hinge during a lamellar keratotomy. For example, when a portion of the cutting head collides with the stop means, the increased load applied to drive motor 21 will trigger a control circuit to stop and/or reverse the direction of motor 21 as desirable for completing the lamellar keratotomy.

The microkeratome may also be equipped with an adjustable float head (not shown) connected to the cutting head for at least partially compressing the cornea ahead of the cutting blade so as to set the corneal resection to the desired shape and thickness. The adjustable float head preferably includes a pair of substantially parallel float arms, and a float having a multi-sided cross-section with multiple respective faces and being supported for rotation between the float arms about a journal that extends through the float. The float head may be equipped with indicia thereon for indicating the resection thickness provided by the selected face.

It is further preferred that each of the faces of the float be spaced at different distances from the journal, whereby the thickness of the corneal resection is varied by rotation of the float until the desired face is in position to compress the cornea. The float may be equipped in various ways, such as by having at least one arcuate face and/or one oblique face, whereby different corneal lenticular resections are performed by compressing the cornea with the respective face. The structure of the float head assembly is described more completely in U.S. Pat. No. 5,980,543, the entire contents of which are incorporated herein by reference.

Those skilled in the art will appreciate that the present invention will permit the orientation of microkeratome 10 in any direction without colliding with the annexes of the eye. The cutting head assembly permits cutting blade 54 to be moved beneath a cutting plane that would be defined by the upper surface of a typical flat-disc type guide ring. The vertical support assembly also dispenses with the need for a larger surface area required by those systems incorporating external drive gear assemblies. Since microkeratome 10 makes use of only one internal gear system, it requires only a minimum available surface area about the patient's cornea. Thus, the present invention is capable of cutting in all directions because the apparatus has the capacity to cut without surpassing the borders of the guide ring assembly.

A surgical procedure is initiated by placing suction ring 13 on the ocular globe in the desired cutting orientation. A vacuum pump (not shown) is activated to attract the cornea to concentric hole 26 of the suction ring at an appropriate pressure to maintain the cornea in a fixed position during the cut. At that time, the lateral support members of shaft 30 are introduced inside the upper slots defined by arm members 20, 22 of vertical support assembly 18, as shown in FIGS. 9A–9B.

Activation of motor 44 advances the instrument so as to first perform a partial flattening of the cornea and then cut the corneal disc as indicated by the sequence of FIGS. 9B–9C. When cutting head 16 collides with a stop means (not shown), the collision produces a voltage drop, triggering a reverse of the current polarity in the motor circuit, and the return of the microkeratome to its place of origin on the guide ring assembly.

Studies have shown that superior, horizontal corneal "hinges," which are achievable through the present invention, are much less likely to experience ablation and traumatic displacement following surgery than a conventional, vertical nasal hinge. Thus, a nasal hinge cannot prevent movement of the corneal flap under the vertical reciprocating motion of the eyelid. A superior or upper hinge, on the other hand, will keep the corneal flap in place under blinking action of the eyelid.

In view of the foregoing it is evident that the present invention is well adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive. The scope of the invention is indicated by the claims that follow rather than the foregoing description, and all changes which come within the meaning and range of equivalence of the claims are therefore intended to be embraced therein.

What is claimed:

1. A microkeratome for performing a lamellar keratotomy of an ocular globe, comprising:
   a guide ring assembly for placement on the ocular globe;
   means for temporarily fixing the guide ring to the ocular globe;
   a cutting head containing a cutting blade suitable for corneal resections; and
   a vertical support assembly connected to said guide ring and supporting said cutting head for rotation about a horizontal axis such that rotation of said cutting head about the horizontal axis moves the cutting blade along an arcuate cutting path into engagement with the cornea of the ocular globe.

2. The microkeratome of claim 1, further comprising means for rotating said cutting head about the horizontal axis to move the cutting blade at least partially through the cornea to create a corneal flap during a lamellar keratotomy.

3. The microkeratome of claim 2, wherein said vertical support assembly includes a pair of members extending upwardly from said guide ring 180° apart from each other.

4. The microkeratome of claim 3, wherein said cutting head includes a support shaft extending laterally therethrough equipped with lateral support members on either end of the support shaft that extend from opposing sides of said cutting head for engagement with the upwardly extending members of said support assembly.

5. The microkeratome of claim 4, wherein the lateral support members of the support shaft are sized and shaped for static engagement with the upwardly extending members of said support assembly, whereby the support shaft is constrained against rotation relative to the lateral support members.

6. The microkeratome of claim 4, wherein the lateral support members of said rotating means are sized and shaped for rotational engagement with the upwardly extending members of said support assembly, whereby the support shaft is free to rotate relative to the lateral support members.

7. The microkeratome of claim 1, wherein said cutting head includes upper and lower portions connected by a hinge that permits said cutting head to be opened for accessing the cutting blade.

8. The microkeratome of claim 5, wherein
   said cutting head includes an opening providing access to the support shaft, and
   said rotating means includes
      a housing adapted for connection to said cutting head at the opening therein,
      an output shaft rotatably carried within the housing and having an outer portion extending from the housing for passage through the opening in said cutting head and engagement with the support shaft when the housing is connected to said cutting head, and
      means carried within the housing for applying a torque to the output shaft, whereby the application of torque from the torque applying means to the output shaft induces rotation of said cutting head and the housing about the support shaft at a controlled speed.

9. The microkeratome of claim 6, wherein said rotating means includes a housing connected to said cutting head and adapted for gripping by a surgeon to manually induce rotation of said cutting head about the horizontal axis.

10. The microkeratome of claim 2, wherein said rotating means includes means for inducing oscillatory motion in the cutting blade of said cutting head that is transverse the cutting path defined by rotation of said cutting head about the horizontal axis.

11. A method of performing corneal resections for a lamellar keratotomy, comprising:
   supporting a cutting head carrying a cutting blade for rotation about a horizontal axis elevated above the patient's eye; and
   inducing rotation of the cutting head about the horizontal axis to move the cutting blade through a pendular cutting path that intersects the cornea.

12. The method of claim 11, wherein the cutting head is supported by fixing a guide ring to an ocular globe about the globe's cornea so that the cornea extends through and above the guide ring, the guide ring including a support system extending upwardly therefrom, and the cutting head including a support shaft adapted for alignment with the horizontal axis and constrained against rotation about the horizontal axis by the support system when the support shaft is placed in engagement with the support system.

13. The method of claim 12, wherein rotation is induced by the operating a motor to apply a torque to the constrained support shaft to drive the cutting head and move the cutting blade through a pendular cutting path that intersects the cornea.

14. The method of claim 11, further comprising the step of stopping the movement of the cutting blade at a predetermined point along the cutting path whereby a hinged corneal cap is formed.

15. A method of performing corneal resections for a lamellar keratotomy, comprising the steps of:

fixing a guide ring to an ocular globe about the globe's cornea so that the cornea extends through and at least partially above the guide ring; and applying torque to a cutting head carrying a cutting blade and supported for rotation about a horizontal axis elevated above the guide ring by a support system extending vertically from the guide ring, whereby the torque applied to the cutting head moves the cutting blade through a pendular cutting path that intersects the cornea.

16. A microkeratome for performing a lamellar keratotomy of an ocular globe, comprising:

a guide ring assembly for placement on the ocular globe such that the globe's cornea protrudes there through;

means for temporarily fixing the guide ring to the ocular globe;

a cutting head containing a cutting blade suitable for corneal resections; and a vertical support assembly connected to said guide ring and supporting said cutting head for rotation about a horizontal axis elevated above said guide ring.

* * * * *